(12) United States Patent
Gallagher et al.

(10) Patent No.: US 7,850,922 B2
(45) Date of Patent: Dec. 14, 2010

(54) FLUID SAMPLE COLLECTION SYSTEM

(75) Inventors: Timothy Joseph Gallagher, Auburn, AL (US); Jeffrey H. Steiger, Auburn, AL (US); Robert Hanne, Auburn, AL (US)

(73) Assignee: Capitol Vial Inc., Auburn, AL (US)

( * ) Notice: Subject to any disclaimer, the term of this patent is extended or adjusted under 35 U.S.C. 154(b) by 326 days.

(21) Appl. No.: 12/030,600

(22) Filed: Feb. 13, 2008

(65) Prior Publication Data

US 2009/0202393 A1  Aug. 13, 2009

(51) Int. Cl.
*B01L 99/00* (2010.01)
*B01L 3/00* (2010.01)
*B01L 3/02* (2010.01)

(52) U.S. Cl. ............ 422/101; 422/56; 422/58; 422/99; 422/102; 436/174; 436/176; 436/177; 436/178; 436/180

(58) Field of Classification Search .......... 422/56, 422/58, 99, 101, 102
See application file for complete search history.

(56) References Cited

U.S. PATENT DOCUMENTS

| | | | |
|---|---|---|---|
| 3,776,220 A | 12/1973 | Monaghan |
| 4,014,322 A | 3/1977 | Shah |
| D256,053 S | 7/1980 | Steigerwald |
| 4,278,437 A | 7/1981 | Haggar |
| 4,653,510 A | 3/1987 | Koll |
| 4,749,655 A | 6/1988 | Monthony et al. |
| 4,774,962 A | 10/1988 | Hebel et al. |
| 4,783,056 A | 11/1988 | Abrams |
| 4,803,998 A | 2/1989 | Kezes et al. |
| 4,812,116 A | 3/1989 | Abrams |
| 4,877,036 A | 10/1989 | Saint-Amand |
| 5,000,193 A | 3/1991 | Heelis et al. |
| 5,091,316 A | 2/1992 | Monthony et al. |
| 5,133,470 A | 7/1992 | Abrams et al. |
| 5,151,094 A | 9/1992 | Hanifl |
| 5,246,856 A | 9/1993 | Gaarslev |
| 5,268,148 A | 12/1993 | Seymour |
| 5,334,502 A | 8/1994 | Sangha |

(Continued)

OTHER PUBLICATIONS

Sarstedt AG & Co., Salivette, Medical and Diagnostic Products [on line], 2003. Retrieved from the Internet: http://www.sarstedt.com/php/main.php?newlanguage=en (2 pages).

(Continued)

*Primary Examiner*—Brian J Sines
(74) *Attorney, Agent, or Firm*—Wood, Herron & Evans, LLP

(57) ABSTRACT

A fluid sample collection system includes a vial, a plunger and a fluid sample collection device having an absorbent for absorbing and retaining a fluid sample therein. The plunger includes an elongated handle portion and a plunger head portion detachably connected to the handle portion. The plunger also includes a splash guard supported on the handle portion. During the sample collection process, the saturated absorbent from the sample collection device is placed into the vial and the plunger is then advanced toward a closed end of the vial to express the fluid sample from the absorbent. The plunger head portion is retained within the vial with the absorbent in a generally compressed state and the handle portion is detached and removed from the vial.

20 Claims, 12 Drawing Sheets

U.S. PATENT DOCUMENTS

| | | | |
|---|---|---|---|
| 5,380,492 | A | 1/1995 | Seymour |
| 5,393,496 | A | 2/1995 | Seymour |
| 5,477,863 | A | 12/1995 | Grant |
| 5,627,071 | A | 5/1997 | Triva |
| 5,723,085 | A | 3/1998 | Abrams et al. |
| 5,830,410 | A | 11/1998 | Thieme et al. |
| 5,979,804 | A | 11/1999 | Abrams et al. |
| 6,021,681 | A | 2/2000 | Jezek |
| 6,176,836 | B1 | 1/2001 | Trudil et al. |
| 6,245,037 | B1 | 6/2001 | Reum et al. |
| 6,303,064 | B1 | 10/2001 | Abrams et al. |
| RE37,676 | E | 4/2002 | Abrams et al. |
| 6,398,067 | B1 | 6/2002 | Belfance et al. |
| 6,406,451 | B1 | 6/2002 | Rowe |
| 6,440,087 | B1 | 8/2002 | Sangha |
| 6,489,172 | B1 | 12/2002 | Bachand et al. |
| 6,514,224 | B1 | 2/2003 | Anapliotis |
| 6,524,530 | B1 | 2/2003 | Igarashi et al. |
| 6,531,096 | B1 | 3/2003 | Deveney et al. |
| 6,592,280 | B2 | 7/2003 | Petrich et al. |
| D483,496 | S | 12/2003 | Kjendlie |
| 6,705,463 | B1 | 3/2004 | Bucholtz et al. |
| 6,740,049 | B2 | 5/2004 | Wallach |
| 6,769,558 | B1 | 8/2004 | Bucholtz |
| 6,840,911 | B2 | 1/2005 | Sangha |
| D507,351 | S | 7/2005 | Birnboim |
| 6,921,395 | B2 | 7/2005 | Carano et al. |
| 7,282,181 | B2 | 10/2007 | Hudak et al. |
| 2001/0039058 | A1 | 11/2001 | Iheme et al. |
| 2002/0136665 | A1 | 9/2002 | Hayton et al. |
| 2002/0197738 | A1 | 12/2002 | Matsumoto et al. |
| 2004/0158188 | A1 | 8/2004 | Kauffmann et al. |
| 2004/0170536 | A1 | 9/2004 | Daykin |
| 2004/0267181 | A1 | 12/2004 | Tuite et al. |
| 2005/0010132 | A1 | 1/2005 | Pestes et al. |
| 2005/0010133 | A1 | 1/2005 | Pestes et al. |
| 2005/0136553 | A1 | 6/2005 | Kaylor et al. |
| 2005/0252820 | A1 | 11/2005 | Sanchez-Felix et al. |
| 2006/0057027 | A1* | 3/2006 | Hudak et al. .......... 422/99 |
| 2007/0208274 | A1 | 9/2007 | Ostrowski et al. |

OTHER PUBLICATIONS

United States Patent and Trademark Office, Office Action, U.S. Appl. No. 11/276,521, mailed Nov. 23, 2009 (34 pages).

United States Patent and Trademark Office, Non-Final Office Action, U.S. Appl. No. 12/364,831, mailed Mar. 30, 2010 (21 pages).

* cited by examiner

FLUID SAMPLE COLLECTION SYSTEM

FIELD OF THE INVENTION

The present invention relates generally to sample collection systems and, more particularly, to a sample collection system for collecting and transporting a fluid sample.

BACKGROUND OF THE INVENTION

Fluid samples are often collected for diagnostics testing including, by way of example, "drugs of abuse" testing, hormone replacement therapy, other diagnostics and clinical testing including HIV screening, environmental sampling, veterinarian sample collection and other similar applications. The substances collected are varied and include, for example, bodily fluids such as saliva, blood, urine, surface moisture from any type of surface including exterior body surfaces, or any other type of fluid that is typically subjected to diagnostics testing.

It is a common practice to use a swab of absorbent material as a collection medium. The swab is often mounted on an end of a collection stick and is supplied in a kit that also contains a container or vial into which the swab and sample are placed for purposes of transportation or analysis. The vial may contain a buffer solution into which the swab with the sample is submerged.

To collect a sample, the swab is brought into contact with the fluid sample to be collected to transfer the sample to the swab. The swab is then placed in the vial and submerged in the buffer solution. There are many variations in the subsequent sample collecting process depending on how the collected sample is to be analyzed. For example, in some applications, the sample is analyzed contemporaneously with it being collected, and that process may be carried out in the vial or a contiguous container. However, in other applications, the vial with the collected sample is sealed and sent to a different location for subsequent analysis.

With known sample collection systems in which a collected sample is to be shipped to a location for analysis, it is known to seal the swab and the collection stick in the vial for transportation to the location of analysis. At the location of analysis, a technician typically uses the collection stick to compress the swab against the bottom of the vial to extract or express the sample from the absorbent swab into the buffer solution. The swab is then removed from the vial and may be discarded. A pipette or other instrument is then introduced into the vial to remove a mixture of the fluid sample and buffer solution from the vial for analysis.

However, it will be appreciated that if the swab is not sufficiently compressed in the vial by the technician to express the sample from the swab, the integrity of the analysis may be compromised. Moreover, requiring the technician performing the analysis to extract the sample from the swab generally increases the cost and complexity of the analysis process and also risks contamination of the sample while the collection stick is being handled.

A sample collection system has recently been developed that overcomes many of the drawbacks and shortcomings of known prior systems for collecting a sample from an absorbent. That sample collection system, described in U.S. Publication No. 2007/0208274, includes a vial and a collection stick. The vial has a wall defining a closed end and an open end and may be configured to contain an optional buffer solution within the vial. A cap is provided to selectively seal with the open end of the vial.

The collection stick has an elongated handle portion and an absorbent head portion detachably connected to the handle portion. The absorbent head portion is configured to absorb and retain the fluid sample within the absorbent head portion prior to insertion of the collection stick within the vial.

The vial wall and the absorbent head portion are configured to permit insertion of the collection stick into the vial so that the absorbent head portion is compressed against the closed end of the vial to express the fluid sample from the absorbent head portion and mix with a buffer solution within the vial if the buffer solution is present within the vial. The elongated handle portion is detached from the absorbent head portion and removed from the vial while the absorbent head portion is retained in a generally compressed state within the vial.

While the sample collection system described in U.S. Publication No. 2007/0208274 overcomes many of the drawbacks and shortcomings of known prior systems for collecting a sample from an absorbent, there is a continuing need for a sample collection system that simplifies the extraction of a fluid sample from an absorbent for subsequent analysis of the sample. There is also a continuing need for a sample collection system that assures proper mixing of a fluid sample and buffer solution within a vial for accurate analysis of the sample, with minimal loss or contamination of the sample during the collection process.

SUMMARY OF THE INVENTION

The present invention overcomes the foregoing and other shortcomings and drawbacks of sample collection systems heretofore known for use in collecting and transporting fluid samples for analysis. While the invention will be described in connection with certain embodiments, it will be understood that the invention is not limited to these embodiments. On the contrary, the invention includes all alternatives, modifications and equivalents as may be included within the spirit and scope of the present invention.

In accordance with the principles of the present invention, a sample collection system or kit is provided including a vial, a plunger and a fluid sample collection device having an absorbent for absorbing and retaining a fluid sample therein. The vial has a wall defining a closed end and an open end and may be configured to contain an optional buffer solution within the vial. A cap is provided to selectively seal with the open end of the vial.

According to one aspect of the present invention, the plunger includes an elongated handle portion and a plunger head portion that is detachably connected to the handle portion. During the sample collection process, the saturated absorbent is placed into the vial and may be at least partially submerged in the optional buffer solution. The user thereafter advances the plunger toward the closed end of the vial so that the absorbent is compressed against the closed end of the vial. The compression of the absorbent against the closed end of the vial causes the sample to express from the absorbent and mix with the buffer solution. Following compression of the absorbent, the handle portion is removed from the vial while the plunger head portion is retained within the vial with the absorbent in a generally compressed state.

According to another aspect of the present invention, the plunger includes a splash guard that is supported by the handle portion of the plunger. The splash guard is configured to minimize fluid movement into a space defined between the splash guard and the open end of the vial while the absorbent is being compressed against the closed end of the vial. The splash guard minimizes splashing of the buffer and sample mixture as the absorbent is being compressed to express the sample from the absorbent. The splash guard reduces the potential loss of the collected sample through the open end of the vial and also minimizes potential contamination of the sample during the sample collection process.

The above and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF THE INVENTION

Referring now to the figures, a fluid sample collection system or kit 10 according to one embodiment of the present invention is shown for collecting and transporting a fluid sample for diagnostics testing. By way of example, the fluid sample may comprise saliva, blood, urine, surface moisture from any type of surface including an exterior body surface, or any other type of fluid that is typically subjected to diagnostics testing. For example, the sample collection kit 10 can be used in applications such as "drugs of abuse" testing, hormone replacement therapy, other diagnostics and clinical testing including HIV screening, environmental sampling, veterinarian sample collection and other similar applications.

Figure 1:
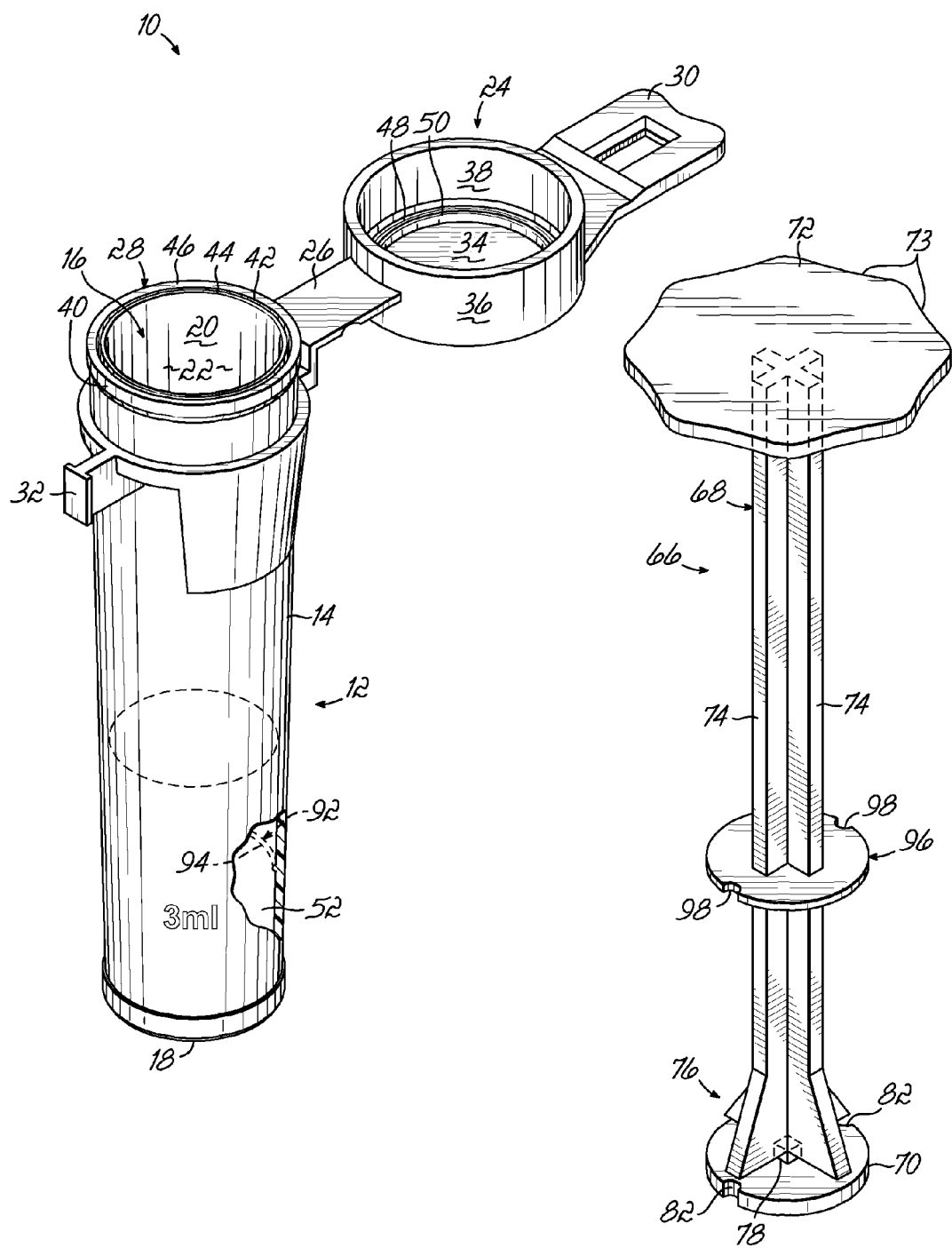
FIG. 1 is a perspective view of a vial and a plunger that may be used in a fluid sample collection system or kit in accordance with one embodiment of the present invention.

As shown in FIG. 1, the sample collection kit 10 includes a vial 12 having a vial wall 14 that defines an open end 16, a closed end 18, and an interior surface 20 extending between the open and closed ends 16, 18 of the vial to form a vial cavity 22. In one embodiment, a cap 24 is connected to the vial 12 by means of a flexible hinge strap or tab 26. As will be described in greater detail below, the cap 24 is configured to form a generally fluid-tight seal with an annular lip 28 provided at the open end 16 of the vial 12 when the cap 24 is closed over the open end 16 during transportation of the vial 12 to and from the collection site as will be described in greater detail below.

Figure 3A:
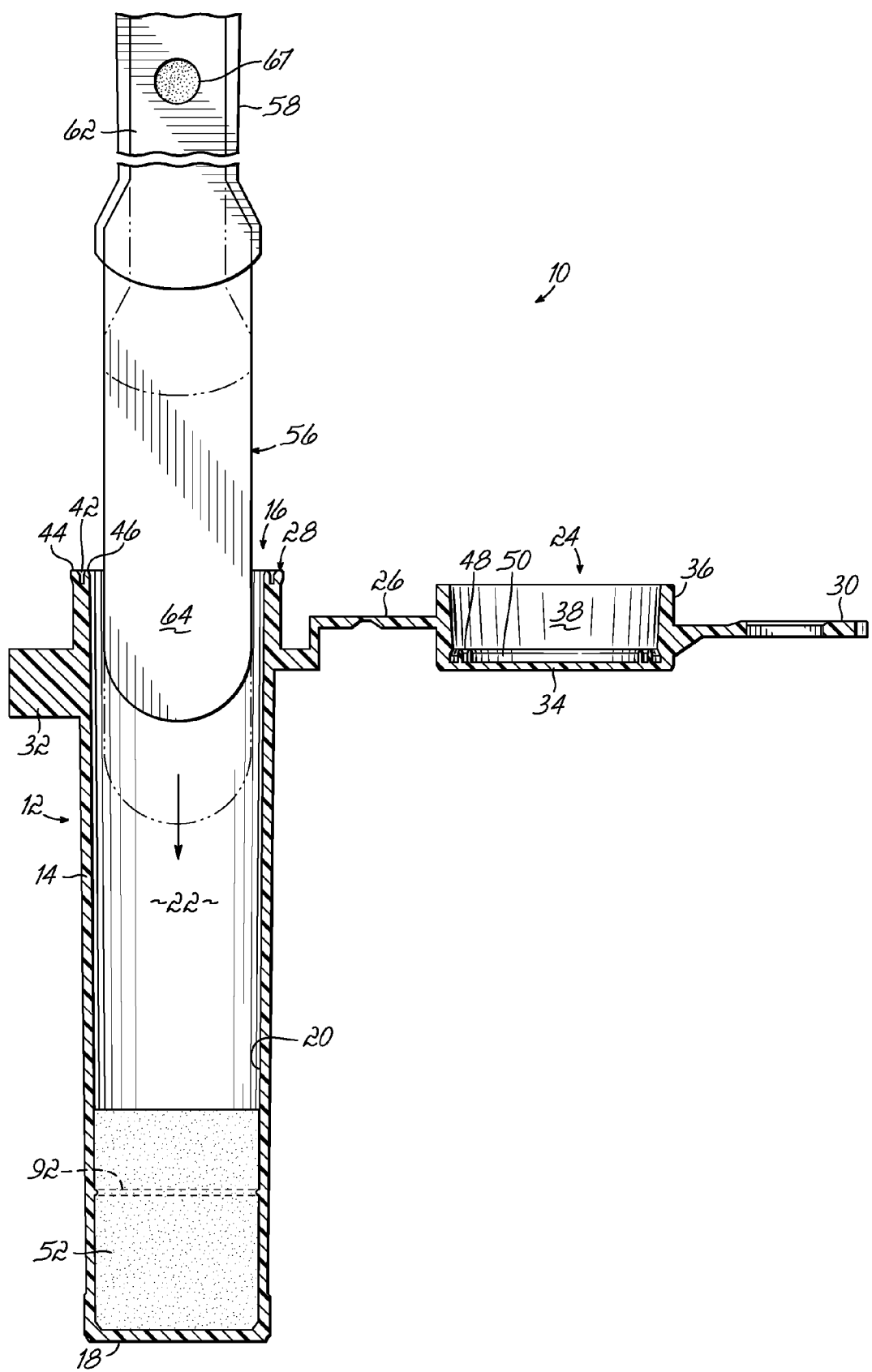
FIGS. 3A-3F are partial cross-sectional views illustrating an exemplary sample collection system or kit and various steps for using the vial and plunger of FIG. 1 and the fluid collection device of FIGS. 2A-2C for collecting a fluid sample and making it available for analysis.
Figure 3B:
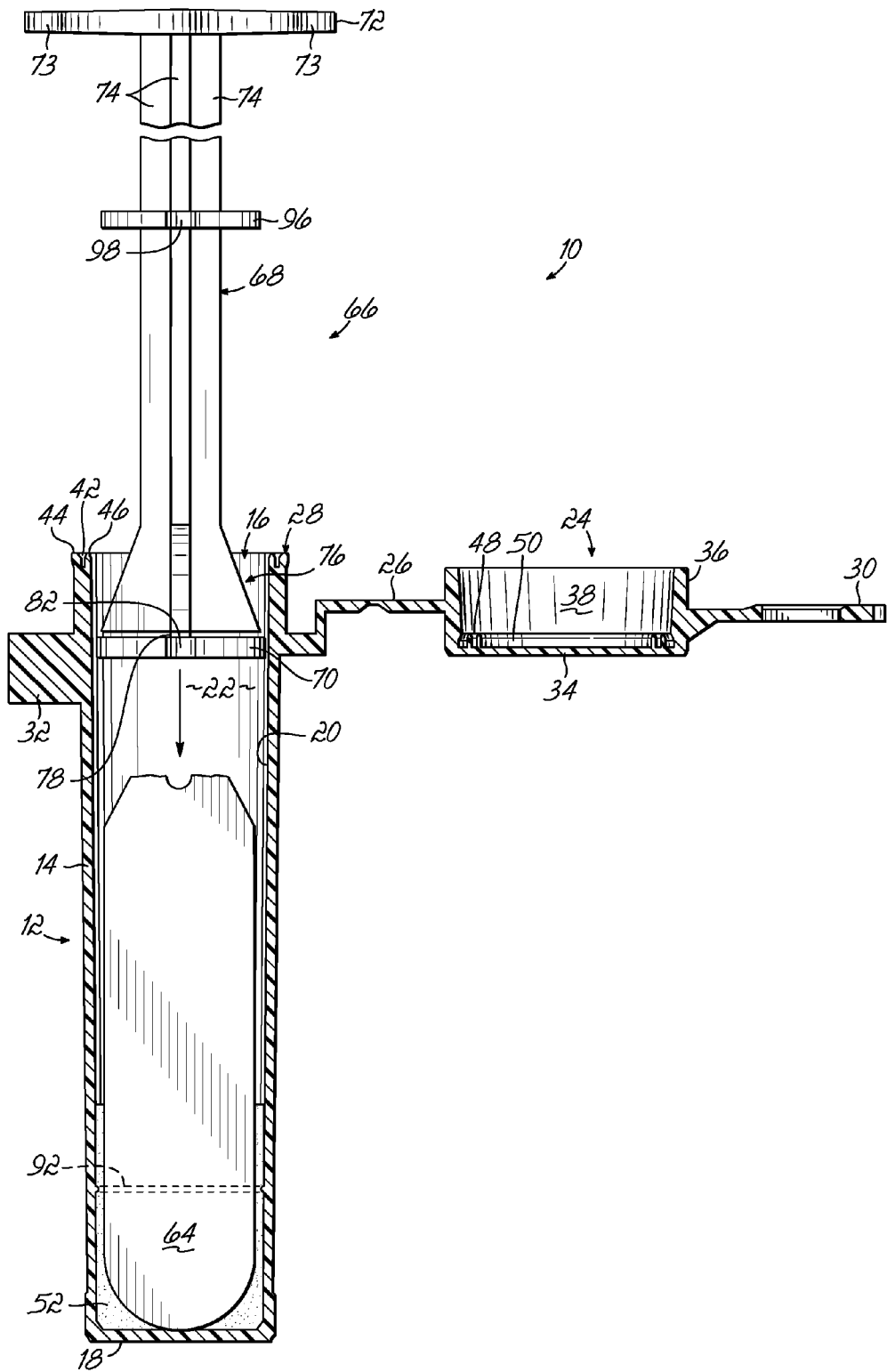
Figure 3C:
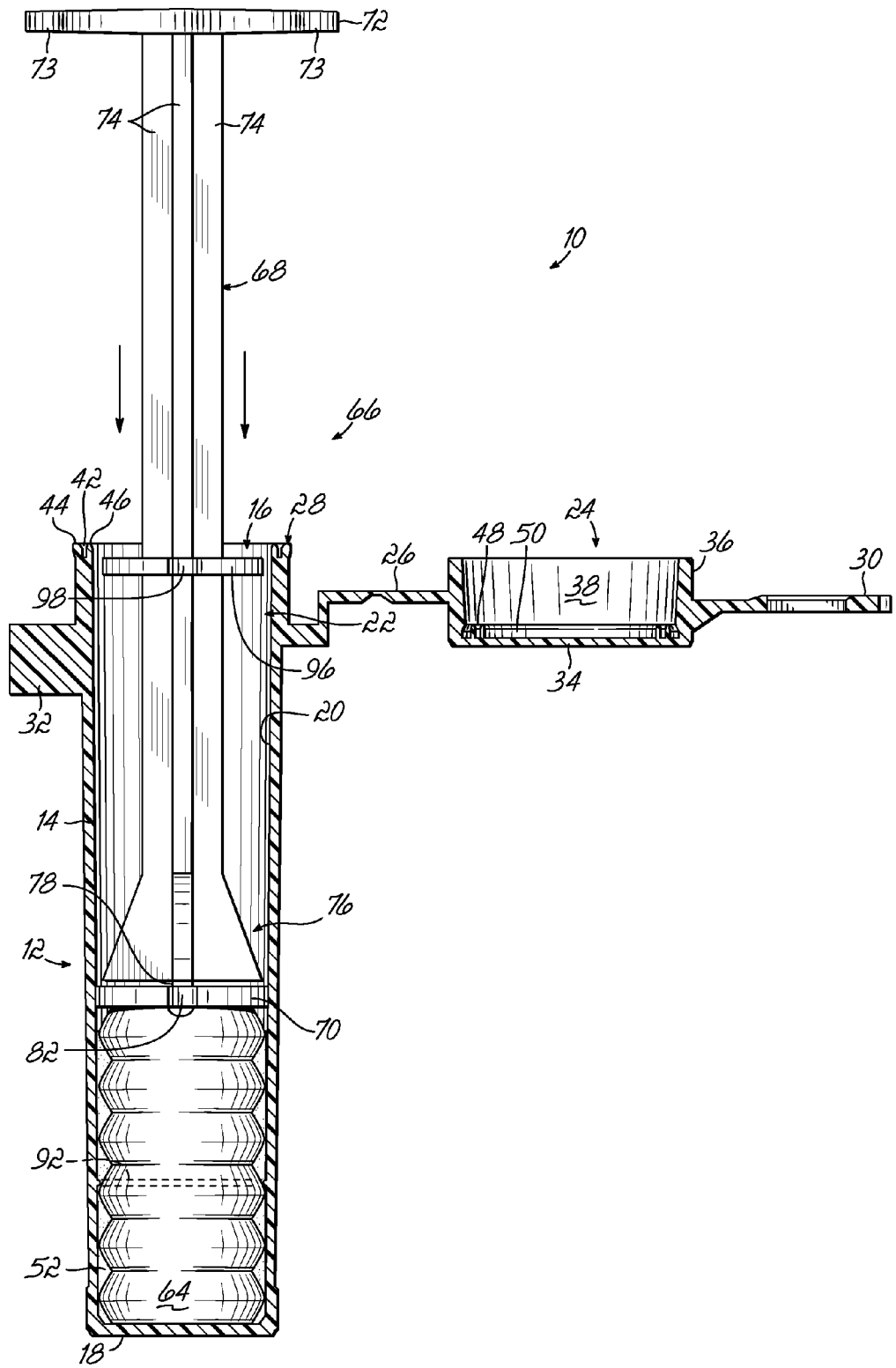
Figure 3D:
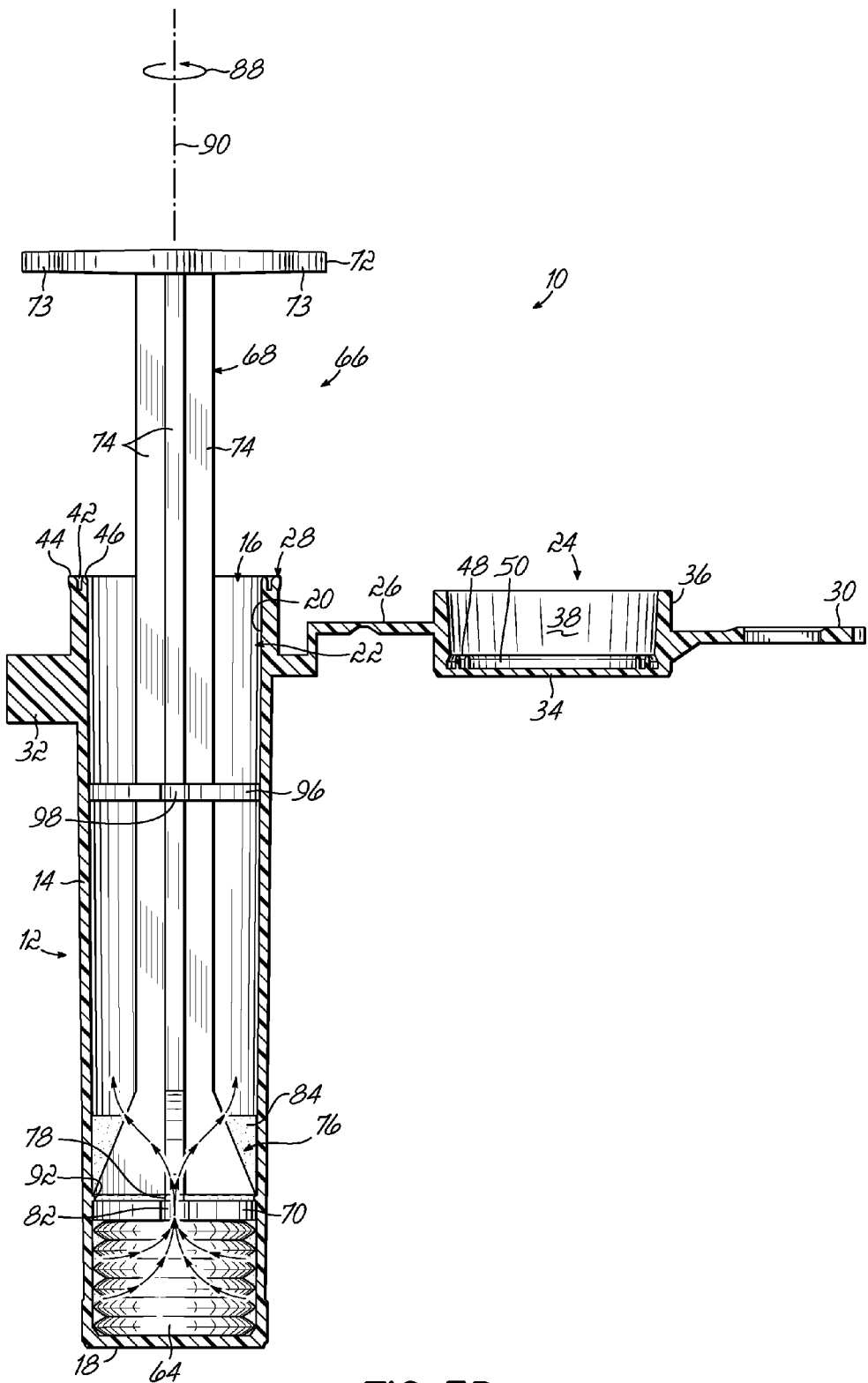
Figure 3E:
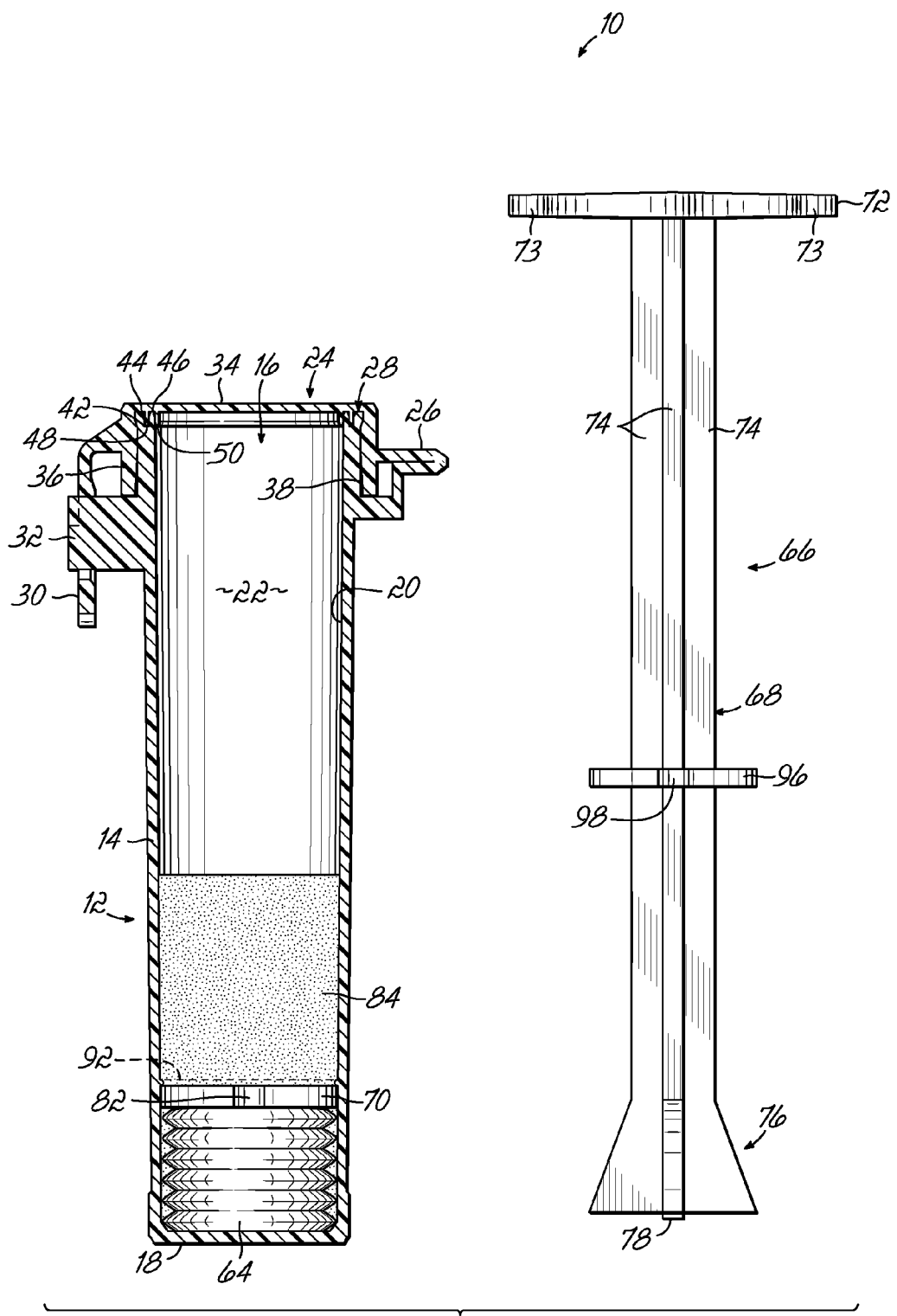

The strap or tab 26 allows the cap 24 to move between an open position as shown in FIGS. 1 and 3A-3C, wherein the cavity 22 within the vial 12 is accessible through the open end 16, and a closed position as shown in FIG. 3E, wherein the cap 24 forms a generally fluid-tight seal with the annular lip 28. An optional locking tab 30 (FIGS. 1 and 3A-3F) may be provided extending outwardly from the cap 24 to engage a locking post 32 provided on the vial 12 when the cap 24 is closed to releasably lock the cap 24 in the closed position as shown in FIG. 3E.

In one embodiment, the cap 24 includes a top wall 34 and a skirt wall 36 depending from the top wall 34. An inner surface 38 of the skirt wall 36 is provided with a contour (see FIG. 1) that is configured to generally form a seal with a contoured outer surface 40 (see FIG. 1) provided on the annular lip 28 when the cap 24 is closed as shown in FIG. 3E.

The vial 12 may include an annular recess 42 (FIG. 1) provided in the annular lip 28 to define an annular inner lip 44 and an annular outer lip 46. The cap 24 may include a pair annular sealing flanges 48 and 50 that depend from the top wall 34. The first sealing flange 48 is configured to be received within the recess 42 formed in the lip 28 of the vial 12 when the cap 24 is closed over the open end 16 and generally form a seal with the inner lip 44. The second sealing flange 50 is configured to be received within the vial body adjacent the inner lip 44 and generally form a seal with an inner surface of the inner lip 44 when the cap 24 is closed over the open end 16. The sealing structure is intended to provide leak-proof characteristics at higher levels of internal pressure so that liquid samples contained within the vial 12 may be transported by air.

The exemplary embodiment of the sealing structure provided on the vial 12 is fully described in co-pending U.S. Ser. No. 11/463,721, owned by the common assignee and hereby incorporated herein by reference in its entirety, to which the reader is referred. It will be appreciated that other sealing structures are possible as well without departing from the spirit and scope of the present invention.

The vial 12, cap 24 and strap or tab 26 may be made of plastic or other suitable material and may be integrally molded as a single component during a molding operation as will be understood by those of ordinary skill in the art. For example, the vial 12, cap 24 and strap or tab 26 may be made of polypropylene, polyethylene, polystyrene or any other suitable FDA approved material.

One example of a suitable molding process, which example is not meant to be limiting, is a conventional injection molding process that is disclosed in U.S. Pat. No. RE 37,676 (the entire disclosure of which is incorporated herein by reference). More particularly, as discussed in this patent, molten plastic may be injected through a sprue gate with about fifteen tons of pressure so as to form the product (at the same time, a press may be used to apply about fifteen tons of pressure to a mold). The injected product may be allowed to cool for about six seconds while the temperature thereof drops from about 550° F. to about 100°-120° F. The specific temperature to which the product is formed and the time, prior to opening the mold, may be dependent on numerous factors including the type of plastic, and size and type of product but should be cool enough so that the plastic will retain its shape, and hot enough so that the plastic is not fully set. Water may be circulated through water channels in the mold in order to accelerate the cooling of the product.

In another embodiment, the product may be ejected from the mold using any conventional design known in the art that completely removes the product from the mold without incurring damage thereto. For example, a jet of air may drive an air poppet through its housing until it contacts the product and pushes it from the mold. When the air poppet is projected into the mold cavity, air currents that drive the air poppet may further assist in ejecting the product. The air poppet may be provided with an angled surface that will contact the product in a flat manner so as not to mark the product. In another example, a mechanical pusher may be employed to contact the product and push it out of the mold. In a further example, an ejector sleeve may be employed to push the product out of the mold. In a still further example, a robot mechanism may be employed to remove the product. Additional plastic may then be injected into the mold to repeat the cycle.

Other patents disclosing a mold/molding process, which examples are not meant to be limiting, include U.S. Pat. No. 4,783,056, U.S. Pat. No. 4,812,116 and U.S. Pat. No. 6,303,064 (the entire disclosure of each patent relating to the process of molding of vials is incorporated herein by reference in its entirety).

In one embodiment, the vial 12 is partially filled with a buffer solution 52 up to the level of a fill line (not shown) and the cap 24 is thereafter engaged over the vial open end 16 to seal the vial 12 prior to use of the collection system or kit 10. The optional fill line (not shown) may be printed, molded or otherwise marked or formed on the vial wall 14 to indicate the desired level of buffer solution 52 within the vial 12. Numerical indicia (not shown) may be provided on the vial wall 14 to indicate the volume of buffer solution 52 contained within the vial 12. The vial 12 may be made of a sufficiently translucent material so that the level of buffer solution 52 within the vial 12 may be readily observed through the vial wall 14. Alternatively, the vial 12 may be generally opaque and/or made of a resin providing ultraviolet (UV) protection to prevent change to the fluid sample within the vial 12 due to light exposure.

Figure 2A:
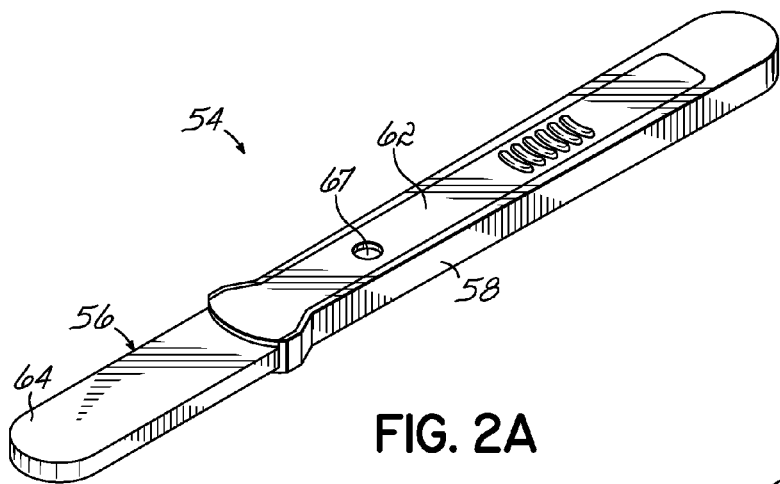
FIGS. 2A-2C are perspective views of an exemplary fluid sample collection device having a handle and an absorbent detachably connected to the handle that may be used in combination with the vial and plunger shown in FIG. 1 as part of the sample collection system or kit.
Figure 2B:
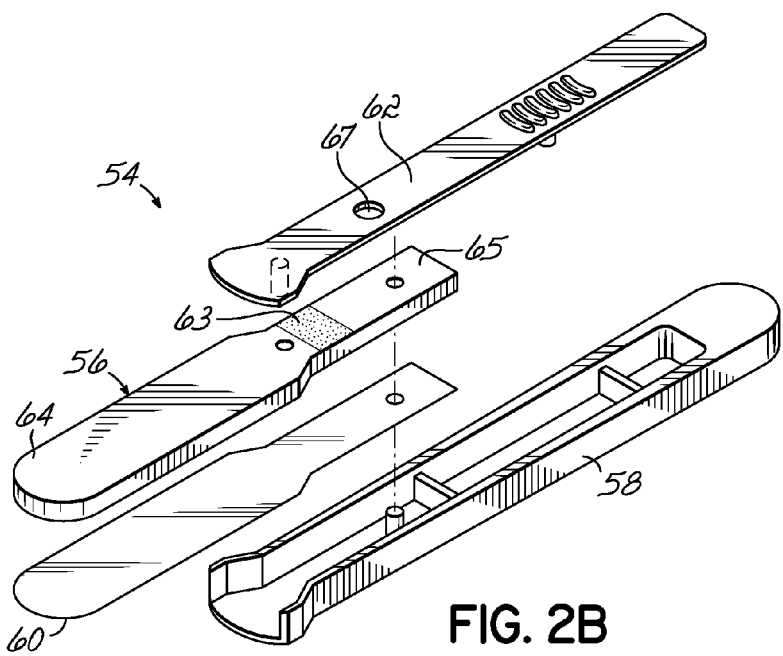
Figure 2C:
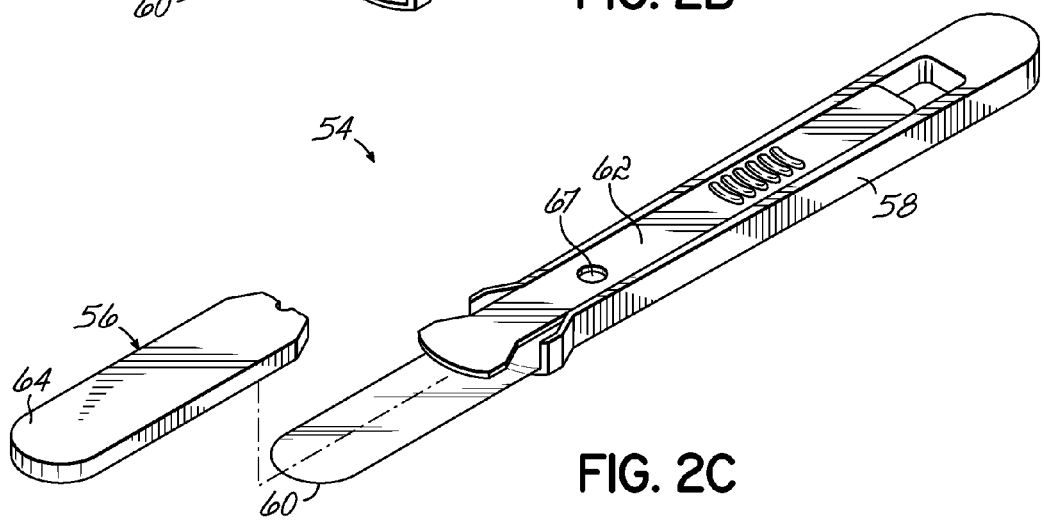

In one embodiment as shown in FIG. 2A-2C, a fluid sample collection device 54 is provided in the collection kit 10 to permit a user to obtain a fluid sample. One suitable fluid collection device 54 for use in the collection kit 10 is fully described in U.S. Pat. No. 6,440,087, hereby incorporated herein by reference in its entirety, to which the reader is referred. Briefly, the sample collection device 54 includes an absorbent pad 56 that is detachably connected to a handle 58. The absorbent pad 56 is comprised of any material that is suitable for collection of a fluid sample, including cellulose fiber such as paper, cotton, nylon or polyester absorbent pads. A plastic guard or shield 60 is provided adjacent a bottom or lower surface of the absorbent pad 56. The plastic guard or shield 60 may be a separate component that is mounted in the handle 58 as shown in FIGS. 2A-2C or, alternatively, the plastic guard or shield 60 may be integrally molded with the handle 58. A separator shaft 62 is slidably mounted on the handle 58 for detaching a forward portion 64 of the absorbent pad 56 from the handle 58 once the fluid sample has been obtained by the user as will be described in greater detail below. It will be appreciated that other types of fluid sample collection devices are possible as well without departing from the spirit and scope of the present invention. Alternatively, it is contemplated that the fluid sample collection device may simply comprise a wad, pad, swab, plug or other suitable mass of absorbent material that is inserted into the vial 12 with a tong or the like after the sample has been obtained by the user.

In one exemplary process of obtaining a sample of saliva using the sample collection device 54, the absorbent pad 56 is placed in a donor's mouth for a time sufficient for the absorbent pad 56 to absorb or collect a sample of the saliva. Thereafter, as shown in FIG. 2C, the separator shaft 62 is pushed forwardly by the user's thumb in the direction of the absorbent pad 56 so that the forward portion 64 of the absorbent pad 56 tears away from a rear portion 65 of the absorbent pad 56 that is captured within the handle 58. The separator shaft 62 is then pulled rearwardly by the user's thumb to reposition the separator shaft 62 within the handle 58.

With the saturated absorbent portion 64 now resting on the plastic shield 60, the user may insert the plastic shield 60 and absorbent portion 64 into the open end 16 of the vial 12 and gently shake the handle 58 so that the absorbent portion 64 is shaken off the shield 60 and into the buffer solution 52 as shown in FIG. 3A. Alternatively, the user may separate the saturated absorbent portion 64 from the shield 60 prior to inserting the absorbent portion 64 into the vial 12. In this instance, the shield 60 of the sample collection device 54 is not inserted into the open end 16 of the vial 12 during the sample collection process. In other embodiments, a saturated wad, pad, swab, plug or other suitable mass of absorbent material containing the fluid sample is inserted into the vial 12 with a tong or the like after the sample has been obtained by the user.

As shown in FIGS. 2B and 2C, the absorbent pad 56 may include a colored vegetable dye 63 provided on a portion of the pad 56 that will migrate along the pad in a direction toward the rear portion 65 as the fluid sample, such as saliva, is absorbed by the pad 56. As shown in FIGS. 2A-2C and FIG. 3A, the separator shaft 62 includes an observation window 67 through which the dye, now dissolved in the saliva, will be visible as the dye migrates toward the rear portion 65 of the absorbent pad 56. The dye 63 and observation window 67 are used to confirm that a sufficient quantity of saliva has been collected in the pad 56 prior to separation of the detachable forward portion 64 of the pad from the handle 58.

In one embodiment, as shown in FIGS. 1 and 3B-3E, the sample collection kit 10 includes a plunger 66 having an elongated handle portion 68 and a plunger head portion 70 detachably connected to the handle portion 68. A handle or thumb tab 72 is provided at one end of the handle portion 68 remote from the plunger head portion 70. In one embodiment, the handle or thumb tab 72 has a generally disk shape and extends radially outwardly from the handle portion 68. The handle or thumb tab 72 may have a series of circumferential indentations 73 so that the handle or thumb tab 72 is designed to be easily grasped by a user's or lab technician's fingers to facilitate insertion of the plunger 66 into the vial 12 and separation of the handle portion 68 from the plunger head portion 70 as described in greater detail below. The handle portion 68 includes a plurality of longitudinally extending ribs 74 that add rigidity to the plunger 66. The ribs 74 flare outwardly near the end 76 of the handle portion 68 to maintain the orientation of the plunger head portion 70 while the plunger 66 is inserted within the vial cavity 22 toward the closed end 18 of the vial 12 as will be described in greater detail below.

In one embodiment, a frangible member 78, such as a pin, is connected between the plunger head portion 70 and the end 76 of the handle portion 68. The frangible member 78 is configured to break or separate upon twisting of the handle portion 68 relative to the plunger head portion 70 so as to permit detachment of the handle portion 68 from the plunger head portion 70 after the plunger 66 has been sufficiently inserted into the vial 12 to express the collected fluid sample from the absorbent 64 so that the sample will mix with the buffer solution 52 as will be described in detail below. The plunger head portion 70 compresses the absorbent 64 against the closed end 18 of the vial 12 as the plunger 66 is advanced within the vial cavity 22.

In one embodiment, the plunger head portion 70 has a generally disk shape as shown in FIG. 1 and remains in the vial 12 following detachment and removal of the handle portion 68 as shown in FIG. 3E. It will be appreciated that other shapes of the plunger head portion 70 suitable for compressing the absorbent 64 are possible as well without departing from the spirit and scope of the present invention. The handle portion 68, plunger head portion 70 and frangible member 78 may be made of plastic or other suitable material and integrally molded as a single component during a molding operation as will be understood by those of ordinary skill in the art. For example, the plunger 66 may be made of polypropylene, polyethylene, polystyrene or any other suitable FDA approved material.

Alternatively, the handle portion 68 and the plunger head portion 70 may be manufactured separately and then connected together through a detachable connection. For example, a mechanical interlock (not shown) may be provided between the end 76 of the handle portion 68 and the plunger head portion 70 so that the handle portion 68 is detachably connected to the plunger head portion 70. Accordingly, it will be appreciated that other methods of detachably connecting the handle portion 68 to the plunger head portion 70 are possible as well without departing from the spirit and scope of the present invention.

The plunger head portion 70 may have a diameter that is generally the same as the inner diameter of the vial 12 generally proximate the closed end 18 so that the plunger head portion 70 frictionally engages the interior surface 20 of the vial 12 generally proximate the closed end 18 when the plunger 66 has been sufficiently inserted into the vial 12 to express the fluid sample from the absorbent portion 64 as described in detail below.

During the sample collection process as shown in FIG. 3B, the absorbent portion 64 is at least partially submerged in the buffer solution 52 and may contact the closed end 18. As the plunger head portion 70 is advanced toward the closed end 18 of the vial 12 via the handle portion 68 of the plunger 66, the absorbent portion 64 is compressed against the closed end 18 of the vial 12 as shown in FIGS. 3C-3D. The compression of the absorbent portion 64 against the closed end 18 of the vial 12 causes the saliva sample to express from the absorbent portion 64 and mix with the buffer solution 52. At the position shown in FIG. 3D, the plunger head portion 70 may frictionally engage with the interior surface 20 of the vial 12 and the absorbent portion 64 is in a generally compressed state.

The plunger head portion 70 may have one or more openings 82 that allow a mixture 84 of the fluid sample and the buffer solution to migrate from the bottom side of the plunger head portion 70 (i.e., the space between the closed end 18 of the vial 12 and the plunger head portion 70) to the opposite upper side as shown in FIG. 3D. For example, as shown FIG. 1, the openings 82 may comprise two peripheral cutouts or slots formed in the plunger head portion 70. It will be appreciated that other configurations of openings 82 are possible as well without departing from the spirit and scope of the present invention.

Following compression of the absorbent portion 64 with the closed end 18 of the vial 12, the handle portion 68 is then twisted in either direction, as represented by arrow 88 in FIG. 3D, to rotate the handle portion 68 about an axial centerline 90. The plunger head portion 70 is prevented from rotating with the handle portion 68 due to its frictional engagement with the vial wall 14. The twisting force applied to the handle portion 68 causes the frangible member 78 to break and thus separate the handle portion 68 from the plunger head portion 70.

As shown in FIG. 3E, the handle portion 68 is then removed from the vial 12 and may be discarded. The plunger head portion 70 is retained within the vial 12 with the absorbent portion 64 in a generally compressed state. The mixture 84 of the fluid sample and the buffer solution is present in the vial 12 above the plunger head portion 70.

Figure 3F:
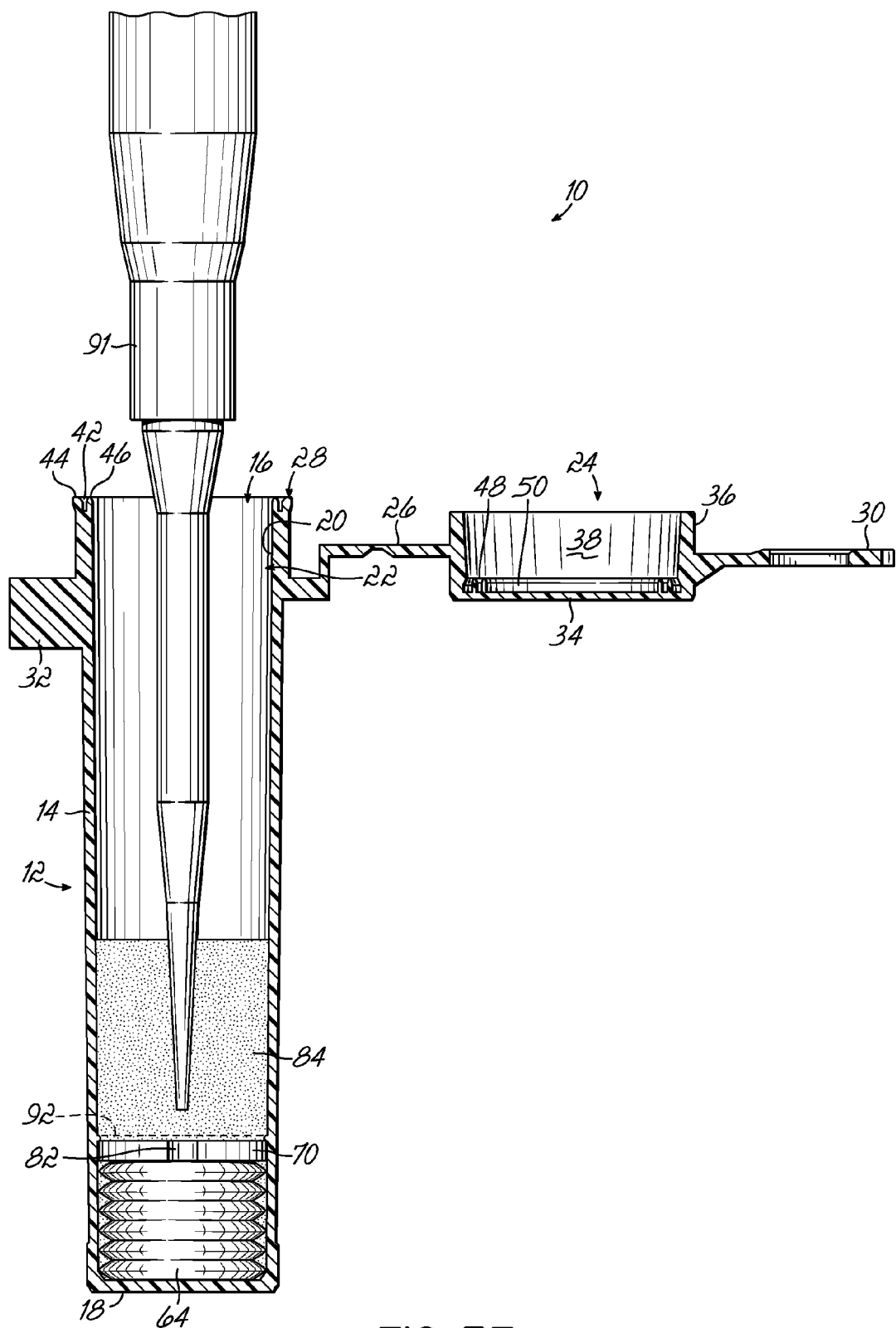

Thereafter, as shown in FIG. 3E, the cap 24 is sealingly engaged with the vial 12 and the vial 12 with the mixture 84 of the fluid sample and buffer solution is then transported to a location where an analysis of the saliva sample is to be performed. At the location of the analysis, as shown in FIG. 3F, the cap 24 is unlocked and opened, and a pipette 91 can be inserted into the vial 12 to collect the mixture 84 of the fluid sample and buffer solution for analysis.

It will be appreciated that other types of mechanical interferences known to those of ordinary skill in the art are possible as well to retain the plunger head portion 70 within the vial 12 while permitting detachment of the handle portion 68 without departing from the spirit and scope of the present invention.

As shown in FIGS. 1 and 3A-3F, a projection 92 may be provided spaced from the closed end 18 of the vial 12 and extending inwardly from the interior surface 20 of the vial wall 14. In one embodiment, the projection 92 comprises a continuous annular rib having a contour that defines an inner diameter at the rib that is slightly smaller than the diameter of the plunger head portion 70. As the plunger head portion 70 is urged toward the closed end 18 of the vial 12 to compress the absorbent portion 64, the plunger head portion 70 engages and rides over the rib. As this occurs, an audible "click" and/or a tactile indication is provided to the user to indicate that the plunger 66 has been sufficiently inserted into the vial 12 to express the fluid sample from the absorbent portion 64. Following receipt of this audible and/or tactile indication, the user then twists and removes the handle portion 68 and the plunger head portion 70 is retained in the vial 12 with the absorbent portion 64 in a generally compressed state. It will be appreciated that other configurations of projections capable of providing an audible and/or tactile indication to a user are possible as well without departing from the spirit and scope of the present invention.

During the sample collection process, it is desirable to minimize splashing of the buffer and sample mixture 84 as the absorbent portion 64 is being compressed against the closed end 18 of the vial 12 using the plunger 66. This reduces the potential loss of the collected sample through the open end 16 of the vial 12 and also minimizes potential contamination of the sample during the sample collection process. According to one aspect of the present invention as shown in FIGS. 1 and 3B-3E, the plunger 66 includes a splash guard 96 that is supported by the handle portion 68 at a position located between the handle or thumb tab 72 and the plunger head portion 70.

In one embodiment, the splash guard 96 has a generally disk shape and extends adjacent the wall 14 of the vial 12 to minimize fluid movement into a space defined between the splash guard 96 and the open end 16 of the vial 12 while the absorbent portion 64 is being compressed against the closed end 18 of the vial 12. The splash guard 96 may have a diameter that is less than an inner diameter of the vial 12 generally proximate a mid-portion of the vial 12. In this way, the splash guard 96 does not frictionally engage the wall 14 of the vial 12 but does stabilize the plunger 66 as it is advanced toward the closed end 18 of the vial 12 to minimize wobbling of the plunger 66. Alternatively, the splash guard 96 may be dimensioned so as to frictionally engage the wall 14 of the vial 12 generally proximate the mid-portion of the vial 12.

It is contemplated that the splash guard 96 may be generally solid or continuous, such as a general disk shape or, alternatively, the splash guard 96 may be discontinuous. By way of example, the splash guard 96 may comprise a disk having openings therein, a plurality of pie-shaped segments located on the same or different planes defining openings therebetween, a mesh-like structure or a spiral member without limitation. It is contemplated that the splash guard 96 may comprise any structure that is suitably configured to minimize fluid movement into the space defined between the splash guard 96 and the open end 16 of the vial 12 while the absorbent portion 64 is being compressed against the closed end 18 of the vial 12. The splash guard 96 may be integrally formed with the plunger 66 or, alternatively, may be formed separately therefrom and thereafter connected to or engaged with the handle portion 68 of the plunger 66.

The splash guard 96 may have one or more openings 98 that allow air within the vial cavity 22 to migrate from the bottom side of the splash guard 96 (i.e., the space between the upper level of the buffer solution 52 and the splash guard 96) to the opposite upper side of the splash guard 96. This minimizes the build-up of air pressure below the splash guard 96 as the plunger 66 is advanced toward the closed end 18 of the vial 12.

In one exemplary embodiment of the present invention, the vial 12 may have a length of about 3.2 in. (about 8.1 cm) between the open and closed ends 16, 18 of the vial. The open end 16 of the vial 12 may have an inner diameter of about 0.5 in. (about 1.3 cm) and the closed end 18 may have an inner diameter of about 0.48 in. (about 1.2 cm). The vial 12 may have an inner diameter of about 0.49 in. (about 1.25 cm) generally proximate a mid-portion of the vial 12. The fill line (not shown) may be located about 0.7 in. (about 1.7 cm) above the closed end 18 of the vial 12. The annular rib 94 may be located about 0.38 in. (about 0.96 cm) above the closed end 18 of the vial 12 and have an axial height of about 0.02 in. (about 0.005 cm) and a radially inward depth of about 0.008 in. (about 0.23 cm) from the interior surface 20 of the vial wall 14. The annular rib 94 may define an inner diameter of about 0.465 in. (about 1.18 cm) at the rib.

The plunger 66 may have length of about 3.2 in. (about 8.1 cm). The plunger head portion 70 may have a thickness of about 0.05 in. (about 0.12 cm) and a diameter of about 0.48 in. (about 1.2 cm). The frangible pin 80 may have a length of about 0.016 in. (about 0.43 cm). The splash guard 96 may have a diameter of about 0.48 in. (about 1.2 cm) and a thickness of about 0.017 in. (about 0.43 cm.). The splash guard 96 may be located about 1.25 in. (about 3.2 cm) above the plunger head portion 70. It will be appreciated that other dimensions and configurations of the vial 12 and plunger 66 are possible as well without departing from the spirit and scope of the present invention.

Figure 4:
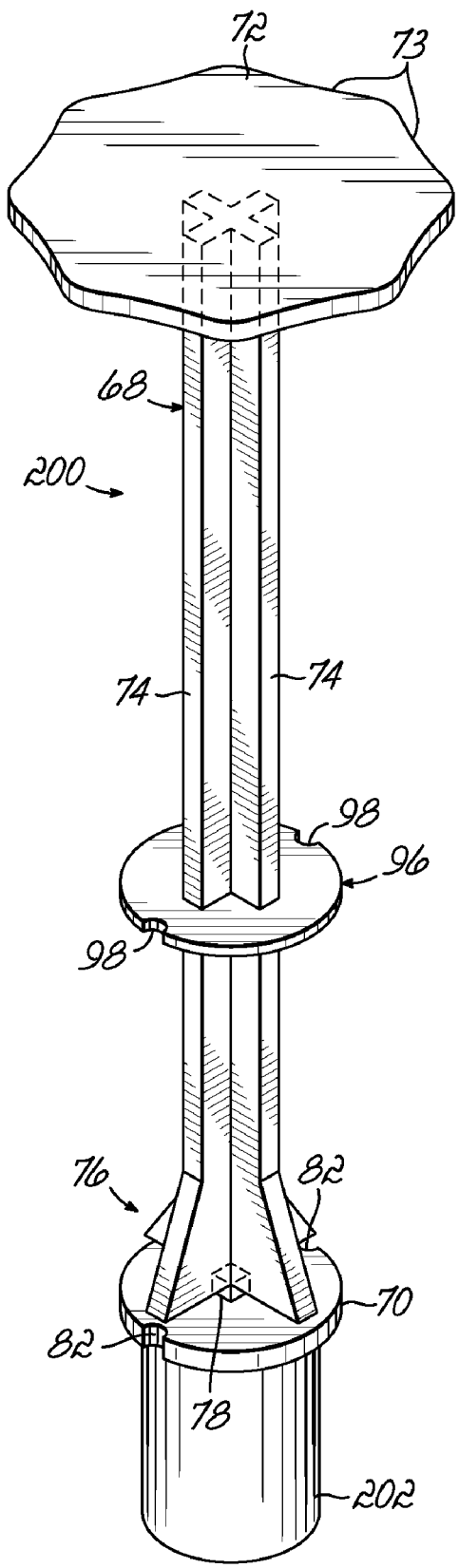
FIG. 4 is a perspective view of a plunger according to another embodiment of the present invention.

Referring now to FIG. 4, a plunger 200 according to an alternative embodiment of the present invention is shown, wherein like numerals refer to like parts as found in the plunger 66 of FIGS. 1 and 3B-3E. In this embodiment, the plunger 200 includes a wad, swab or plug of absorbent material 202 supported by and below the plunger head portion 70. The absorbent material 202 may be operatively connected to the plunger head portion 70 by hot melt adhesive, tape, glue, a mechanical interlock or any other suitable connection method known to those of ordinary skill in the art. Alternatively, it will be appreciated that the plunger head portion 70 and the absorbent material 202 may be integrally formed as a single component without departing from the spirit and scope of the present invention. In this embodiment, a separate sample collection device for obtaining the saliva sample is not required since the absorbent material 202 is provided as part of the plunger 66.

Figure 6:
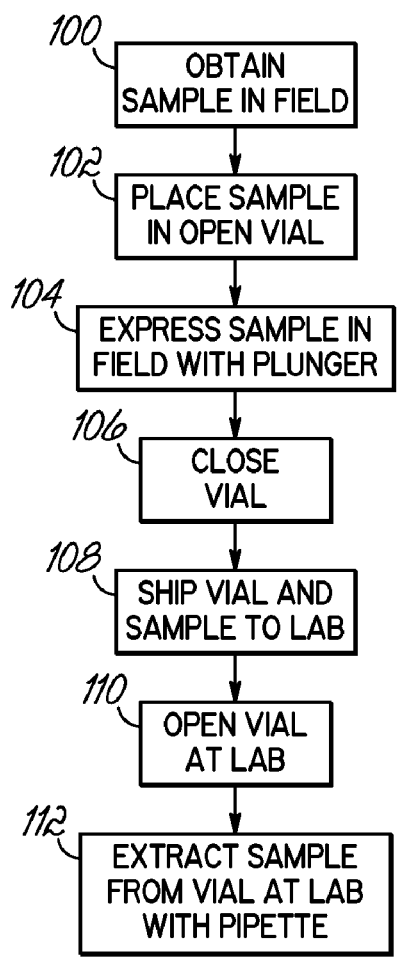
FIG. 6 is a schematic block diagram illustrating various steps for obtaining, expressing and extracting a sample using the sample collection system and kit of the present invention according to one embodiment.

In one embodiment, the sealed and sterilized vial 12 and its associated buffer solution 52, the sterilized fluid sample collection device 54 and the sterilized plunger 66 may be packaged together in kit form for distribution and use. In this instance, as shown schematically in FIG. 6, the user obtains the sample at a first location using the sample collection device 54 as shown at step 100 and places the sample (e.g., the absorbent portion 64) into the open end 16 of the vial 12 as shown at step 102. Using the plunger 66 provided in the kit, the user compresses the absorbent portion 64 against the closed end 18 of the vial 12 as described in detail above to express the sample from the absorbent portion 64 and mix the sample with the buffer solution 52 as shown at step 104. After the plunger 66 has been removed from the vial 12 by the user, the user then closes and optionally locks the vial 12 as shown at step 106. At step 108, the closed vial 12, with the expressed sample contained therein, is then shipped to a second location, such as a laboratory that is remote from the first location of the user, for testing of the sample. During the testing procedure, the vial 12 is opened at the laboratory as shown at step 110, and the sample is then extracted from vial 12 using the pipette 91 or other suitable device as shown at step 112.

Figure 5A:
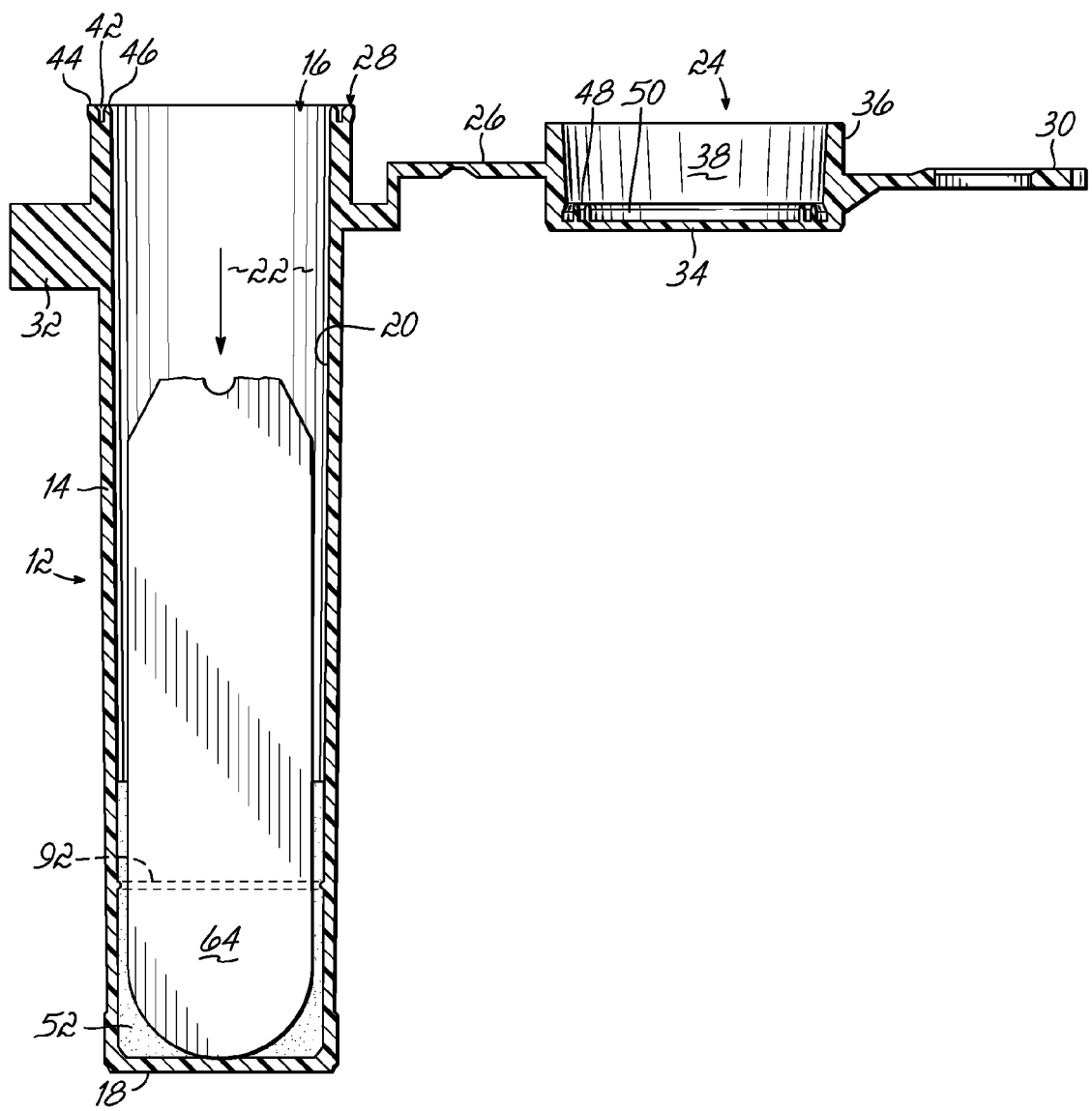
FIGS. 5A-5B are partial cross-sectional views illustrating various alternative steps for using the sample collection system or kit of the present invention.
Figure 5B:
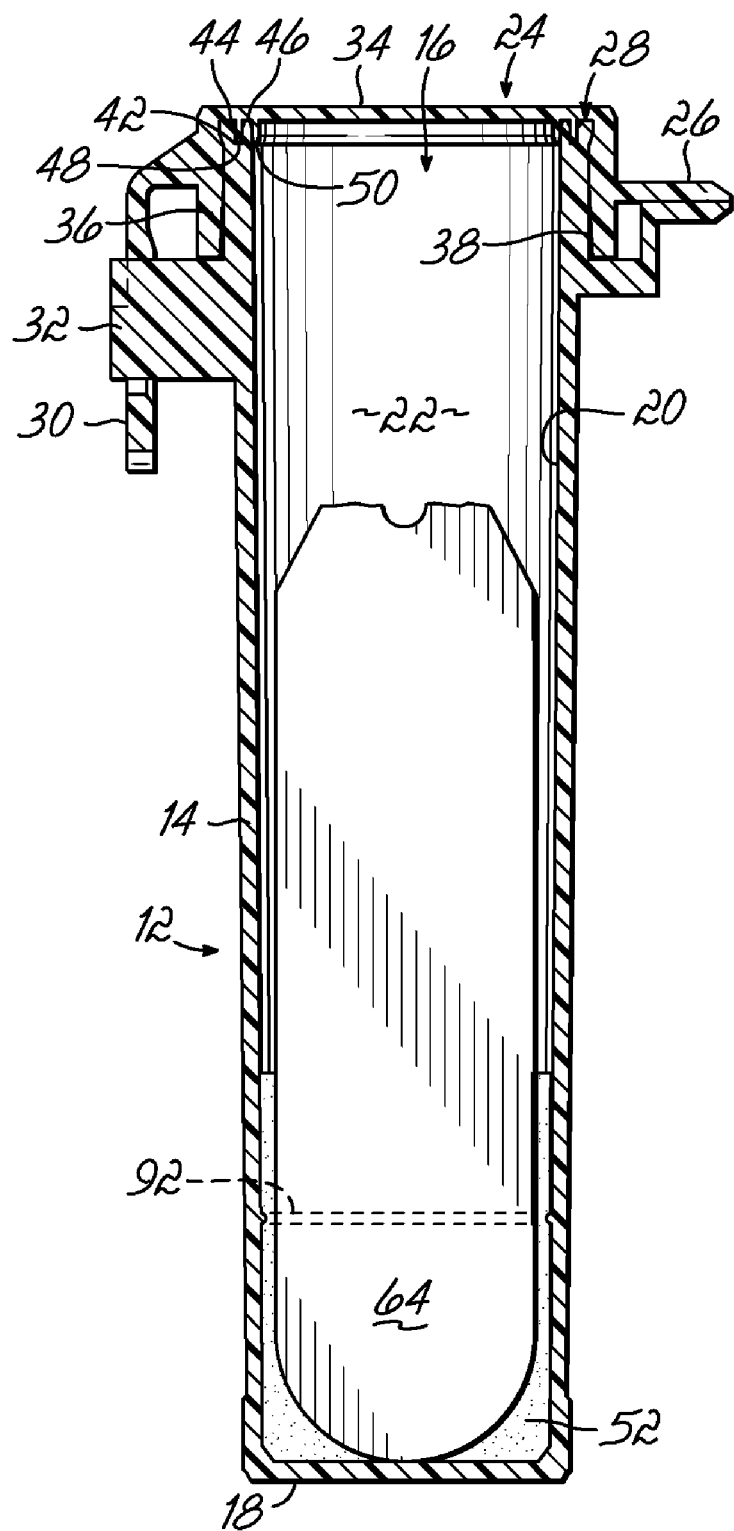
Figure 7:
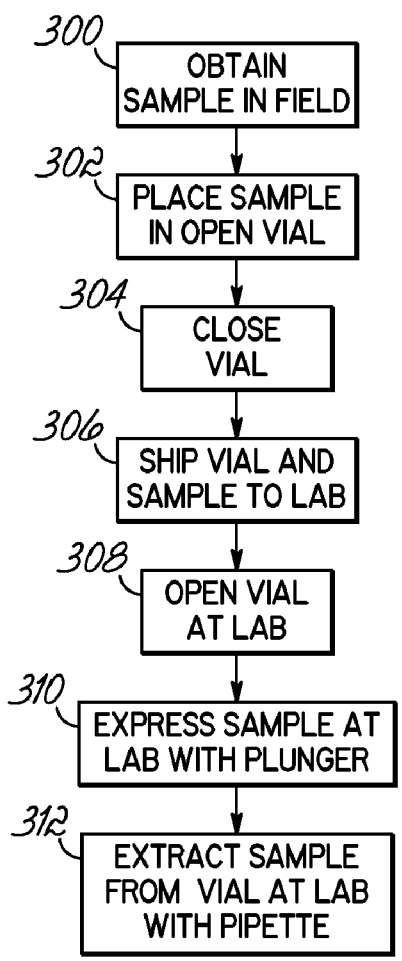
FIG. 7 is a schematic block diagram illustrating various steps for obtaining, expressing and extracting a sample using the sample collection system and kit of the present invention according to an alternative embodiment.

Alternatively, it is contemplated that the sample collection system or kit distributed to the first location may include the sealed and sterilized vial 12 and its associated buffer solution 52 and the sterilized fluid sample collection device 54, but not the plunger 66. In this embodiment, as shown in FIGS. 5A and 7, the user obtains the sample at a first location using the sample collection device 54 as shown at step 300 and places the sample (e.g., the absorbent portion 64) into the open end 16 of the vial 12 as shown at step 302. As shown in FIGS. 5B and 7, the user then closes and optionally locks the vial 12 as shown at step 304. At step 306, the closed vial 12, with the saturated absorbent portion 64 and buffer solution contained therein, is then shipped to a second location, such as a laboratory that is remote from the first location of the user, for testing of the sample. During the testing procedure, the vial 12 is opened at the laboratory as shown at step 308, and the laboratory technician then uses the plunger 66 to compress the absorbent portion 64 against the closed end 18 of the vial 12 as described in detail above to express the sample from the absorbent portion 64 and mix the sample with the buffer solution 52 as shown at step 310. The sample is then extracted from vial 12 using a pipette 91 or other suitable device as shown at step 312.

The sample collection kit 10 of the present invention provides several advantages over known sample collection systems. For example, splash guard 96 provided on the plunger 66 reduces the potential loss of the collected sample through the open end 16 of the vial 12 and also minimizes potential contamination of the sample during the sample collection process. Moreover, since the plunger 66 and the sample collection device 54 are separate components, it is possible for the user to obtain and express the sample at the collection site if the plunger 66 is provided to the user in the kit 10. Alternatively, the user may simply obtain the sample using the vial 12 and sample collection device 54 and return the collected sample to the collection site within the sealed and locked vial 12 so that the sample may be expressed using a plunger 66 at the location of analysis.

The sample collection kit 10 may be used for collecting many different types of fluid samples and therefore, the absorbent material and the buffer solution may vary depending on the needs and requirements of a particular application. For example, while the absorbent material is shown as being a generally flat pad, in other embodiments, it may be hemispherical, straight-sided, fabricated from folded or layered material, etc. Thus, the size and/or shape of the absorbent material is selected based on the diagnostics testing requirements. For example, for collecting a saliva sample, the absorbent material may be a hydrophilic absorbent and selected so as to absorb and release fluids into the buffer solution for testing. In different embodiments, the hydrophilic absorbent may
- include extruded plastic material with a hollow cell configuration, or
- be a material interacting with a buffer solution and/or fluid to be tested, or
- be selected based in part on the desired interference between the absorbent and a fluid, or
- be a material for preventing tetrahydrocannabinol (THC) from binding with the absorbent, or
- include a polyurethane fiber material treated with a surfactant for providing a wicking action, wherein a degree of wicking is based on the amount of saliva or other fluid to be collected for testing purposes, or
- be a material made from at least one of a cotton fiber, a paperboard, plastic or other absorbent material.

The type and/or amount of the buffer solution is selected to interact with a fluid, for example, saliva, to be tested. Typically, the buffer solution resists changes in pH when small quantities of an acid or alkali are added to it. An acid is a compound that donates a hydrogen ion to another compound whereas an alkali is a compound that accepts a hydrogen ion. Thus, generally, there are two types of buffer solutions: an acidic buffer solution having a pH less than 7 and an alkaline buffer solution with a pH greater than 7.

In one embodiment, an acidic buffer solution is a solution for resisting changes in pH, for example, a solution that is made from a weak acid and a corresponding salt, for example, sodium salt. In alternative embodiments, an acidic solution includes a mixture of ethanolic acid and sodium ethanolate. An acidic buffer solution containing equal molar concentrations of both the acid and the salt has a pH of approximately 4.76. The buffer solution can be changed by changing the ratio of acid to salt, or by choosing a different acid and one of its salts.

In another embodiment, an alkaline buffer solution is a solution for resisting changes in pH, for example, a solution that is made from a weak base and a corresponding salt. An alkaline solution may include a mixture of an ammonia solution and ammonium chloride solution. In this embodiment, an alkaline buffer solution having equal molar proportions of this base and acid has a pH of approximately 9.25. In acidic and alkaline solutions, the concentration of the mixture is independent of the amount of mixture as long as the concentration is the same.

In an alternative embodiment of the present invention, a buffer solution 52 is not contained within the vial 12 when the fluid sample is introduced into the vial 12. In this alternative embodiment, the fluid sample collection device 54 may be used to collect a fluid sample as described in detail above. The plunger 66 is inserted through the open end 16 of the vial 12 and advanced within the vial cavity 22 toward the closed end 18. As the user continues to urge the plunger head portion 70 toward the closed end 18 via the handle portion 68 of the plunger 66, the absorbent portion 64 is compressed against the closed end 18 of the vial 12. The compression of the absorbent portion 64 against the closed end 18 of the vial 12 causes the fluid sample to express from the absorbent portion 64 and flow through the openings 82 into the vial cavity 22 where it can be later analyzed at the analysis site. The plunger head portion 70 is retained within the vial 12 with the absorbent portion 64 in a generally compressed state as described in detail above.

While the present invention has been illustrated by description of various embodiments and while those embodiments have been described in considerable detail, it is not the intention of applicant to restrict or in any way limit the scope of the appended claims to such details. Additional advantages and modifications will readily appear to those skilled in the art. The invention in its broader aspects is therefore not limited to the specific details and illustrative examples shown and described. Accordingly, departures may be made from such details without departing from the spirit or scope of applicants' invention.

What is claimed is:

1. An apparatus for containing a fluid sample that is collected on an absorbent, comprising:
    a vial having a wall defining a closed end and an open end;
    a cap configured to selectively seal with the open end of the vial;
    a plunger having an elongated handle portion and a plunger head portion connected to the handle portion, the plunger head portion being configured to compress the absorbent, when it is placed into the vial, into contact with the closed end of the vial to thereby express the fluid sample from the absorbent into the vial; and
    a splash guard supported by the handle portion of the plunger and extending adjacent the wall of the vial to minimize fluid movement into a space defined between the splash guard and the open end of the vial while the absorbent is being compressed into contact with the closed end of the vial.

2. The apparatus of claim 1 wherein the splash guard has a generally disk shape.

3. The apparatus of claim 1 wherein the plunger head portion has a generally disk shape.

4. The apparatus of claim 1 further comprising a frangible member configured to detachably connect the plunger head portion to the handle portion of the plunger.

5. The apparatus of claim 1 wherein the vial has an inner diameter that decreases along at least a partial length of the vial in a direction from the open end toward the closed end of the vial.

6. The apparatus of claim 1 wherein the splash guard has a diameter that is lesser than an inner diameter of the vial generally proximate a mid-portion of the vial.

7. The apparatus of claim 1 wherein the plunger head has a diameter that is generally the same as an inner diameter of the vial generally proximate the closed end of the vial so as to create a frictional interference between the plunger head portion and the vial to permit detachment of the handle portion from the plunger head portion and retention of the absorbent in a generally compressed state within the vial.

8. The apparatus of claim 1 further comprising a buffer solution contained within the vial.

9. The apparatus of claim 1, further comprising an absorbent supported by the plunger head portion.

10. The apparatus of claim 1, wherein the splash guard includes at least one opening configured to permit air to migrate from one side of the plunger head portion to an opposite side thereof.

11. The apparatus of claim 1, wherein the plunger includes a thumb tab extending radially outwardly from the handle portion.

12. The apparatus of claim 11, further comprising a plurality of indentations disposed about the circumference of the thumb tab.

13. A plunger for use with a vial and an absorbent to collect a fluid sample, the absorbent being configured to absorb and retain the fluid sample therein, comprising:

an elongated handle portion;

a plunger head portion connected to the handle portion, the plunger head portion being configured to compress the absorbent, when it is placed into the vial, into contact with the closed end of the vial to thereby express the fluid sample from the absorbent into the vial; and a splash guard supported by the handle portion of the plunger and extending adjacent the wall of the vial to minimize fluid movement into a space defined between the splash guard and the open end of the vial while the absorbent is being compressed against the closed end of the vial, the splash guard being located on the handle portion of the plunger closer to a mid-point of the handle portion than to the plunger head portion.

14. The apparatus of claim 13 wherein the splash guard has a generally disk shape.

15. The apparatus of claim 13 wherein the plunger head portion has a generally disk shape.

16. The apparatus of claim 13 further comprising a frangible member configured to detachably connect the plunger head portion to the handle portion of the plunger.

17. The apparatus of claim 13, further comprising an absorbent supported by plunger head portion.

18. The apparatus of claim 13, wherein the splash guard includes at least one opening configured to permit air to migrate from one side of the plunger head portion to an opposite side thereof.

19. The apparatus of claim 13, wherein the plunger includes a thumb tab extending radially outwardly from the handle portion.

20. The apparatus of claim 19, further comprising a plurality of indentations disposed about the circumference of the thumb tab.

\* \* \* \* \*

UNITED STATES PATENT AND TRADEMARK OFFICE
CERTIFICATE OF CORRECTION

PATENT NO.       : 7,850,922 B2
APPLICATION NO.  : 12/030600
DATED            : December 14, 2010
INVENTOR(S)      : Timothy Joseph Gallagher et al.

Page 1 of 1

It is certified that error appears in the above-identified patent and that said Letters Patent is hereby corrected as shown below:

In column 12, line 10, change "of applicant to restrict" to --of applicants to restrict--.

In column 14, line 9, claim 17, change "supported by plunger head portion." to --supported by the plunger head portion.--.

Signed and Sealed this
First Day of March, 2011

David J. Kappos
*Director of the United States Patent and Trademark Office*